United States Patent [19]

Wong

[11] 4,163,696

[45] Aug. 7, 1979

[54] DISTILLATION PROCESS FOR RECOVERY OF METHYL ISOBUTYL KETONE

[75] Inventor: Wang-Mo Wong, Matteson, Ill.

[73] Assignee: Arthur G. McKee & Company, Independence, Ohio

[21] Appl. No.: 913,530

[22] Filed: Jun. 7, 1978

[51] Int. Cl.² .................. B01D 3/36; C07C 49/06
[52] U.S. Cl. ...................... 203/44; 203/66; 260/593 P
[58] Field of Search ............ 203/44, 43, 66, 50–70; 260/593 R

[56] References Cited

U.S. PATENT DOCUMENTS

| | | | |
|---|---|---|---|
| 2,265,220 | 12/1941 | Sullivan | 203/66 |
| 2,419,521 | 4/1947 | Waldron | 203/66 |
| 2,428,467 | 10/1947 | Petry et al. | 203/66 |
| 2,483,625 | 10/1949 | Cubicciotti | 203/44 |
| 3,265,592 | 8/1966 | Van Der Weel | 260/593 P |

Primary Examiner—Wilbur L. Bascomb, Jr.
Attorney, Agent, or Firm—Bosworth, Sessions & McCoy

[57] ABSTRACT

There is disclosed an azeotropic distillation process for separating toluene from methyl isobutyl ketone (MIBK) in a spent liquor mixture. A toluene azeotrope former, preferably methanol, is added to the liquor in an amount sufficient to form an azeotrope with all of the toluene present in the mixture. The methanol is added in an amount of at least about 2.62, typically an excess amount of about 3.4 to about 6.3 parts by weight of methanol per 1.0 part by weight of toluene. The resulting azeotrope of methanol and toluene is then separated by distillation from the MIBK. The methanol may be subsequently recovered from the toluene by extraction with water. Other toluene azeotrope formers may be utilized.

12 Claims, 1 Drawing Figure

DISTILLATION PROCESS FOR RECOVERY OF METHYL ISOBUTYL KETONE

DISCLOSURE OF THE INVENTION

1. Field of the Invention

This invention relates to a process for separating and recovering organic liquids in a spent liquor mixture. More particularly, this invention relates to an azeotropic distillation process for separating toluene from methyl isobutyl ketone, hereinafter for convenience referred to as MIBK.

2. Background of the Invention

The separation of toluene from methyl isobutyl ketone (MIBK) is very difficult. Thus, the theoretical distillation separation and recovery of MIBK from a mixture of 96% by weight MIBK, 2% by weight toluene, and 2% by weight $H_2O$ requires a distillation column of at least 56 theoretical plates and a reflux ratio of 27. However, since the resulting overhead contains 18.89% by weight toluene, 60.62% by weight MIBK, and 19.49% by weight $H_2O$, it is apparent that the separation of toluene from MIBK by simple distillation is not feasible.

SUMMARY OF THE INVENTION

It is an object of the invention to provide a distillation process for separating a mixture of MIBK and toluene which comprises adding a toluene azeotrope former to the mixture prior to distillation and then distilling the mixture to separate and recover a first fraction of the MIBK and a second fraction of an azeotrope of the former and toluene.

Preferably, this process is one wherein the azeotrope former is methanol and there is formed an azeotrope of toluene and methanol.

Also preferably, the process is one wherein the methanol or other toluene azeotrope former is added to the spent liquor mixture in an amount at least sufficient to form an azeotrope with all of the toluene present in the mixture.

DESCRIPTION OF THE DRAWINGS

These and other features and aspects of the invention will become apparent from the following disclosure of a preferred process embodying the invention in connection with the accompanying drawing, in which.

DISCLOSURE OF A PREFERRED EMBODIMENT

Figure 1:
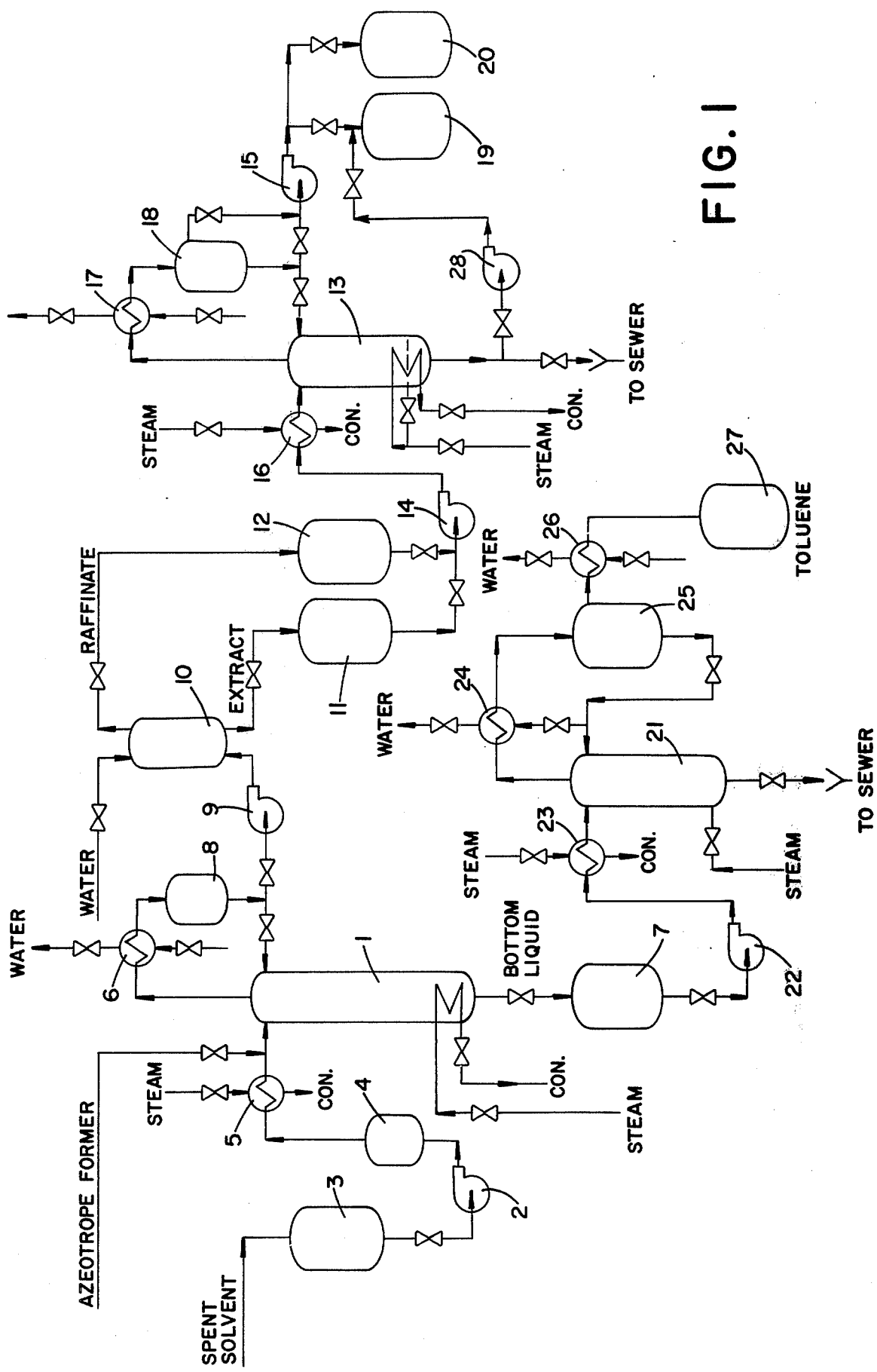
FIG. 1 of the drawing is a schematic flow diagram of a distillation and extraction process that may be utilized in the practice of the invention.

According to a preferred process of the present invention, methyl isobutyl ketone (MIBK) is separated from a mixture of MIBK and toluene by adding a third substance, preferably methanol, as an azeotrope former for the toluene. For a spent solvent mixture containing 96% by weight MIBK, 2% by weight toluene, and 2% by weight water, the solvent is dehydrated with drying agents such as sodium hydroxide, sodium sulfate, silica gel, etc. The dry solvent is then fed into a distillation column with about 12.5 parts by weight of methanol per 98 parts by weight of dry solvent. Toluene-methanol azeotrope along with excess methanol distills off as overhead at a temperature of 60.2° to 64° C. The boiling temperature difference between the azeotrope and the MIBK is about 56° to 57° C. This makes the separation of these streams easy and possible. A portion of the azeotrope is returned to the column as reflux while the remaining liquid is further processed as described hereinafter. With proper design and operation, about 10 to 20 theoretical plates in the column and a reflux ratio of about 10 to 15, a good separation of at least 95% by weight of MIBK is feasible.

Methanol is recovered from the azeotrope by extraction with water. Pure toluene is recovered by distilling the raffinate while methanol is recovered by distilling the extract.

The azeotrope former is added to the spent liquor mixture in an amount sufficient to form an azeotrope with all of the toluene in the mixture. With methanol as the azeotrope former, the methanol is added in an amount of at least about 2.62 parts by weight per 1.0 part by weight toluene. In practice the methanol is added in excess of the required azeotrope forming amount with both the excess methanol and the azeotrope being recovered together as the distillation overhead fraction. Preferably the methanol is added in an excess amount of about 3.4 to about 6.3 parts by weight methanol per 1.0 part by weight toluene.

The following example, discussed with reference to the process flow diagram in the drawing, represents the best embodiment and mode known to and contemplated by the inventor in the practice of this invention. This example and embodiment illustrates the invention in terms of a continuous azeotropic distillation and extraction process.

EXAMPLE

Spent solvent from a pharmaceutical process, containing 96% by weight MIBK, 2% by weight water and 2% by weight of toluene and a trace of non-volatile organic material is used as feed. It is fed into a rectifying column 1 of approximately 15 theoretical plates by pump 2 from tank 3 through a dryer 4 and a heater 5. The dryer 4 is packed with dehydrating agent, such as silica gel, which is used to remove water from the feed. The resulting liquor is allowed to preheat to about 60° C. with steam before it flows into column 1. At the inlet to column 1, a stream of azeotrope former methanol is added to the liquor at a rate of 12.5 parts by weight methanol per 98 parts by weight of dry feed. An overhead, containing an azeotrope mixture of 27.6% by weight toluene and 72.4% by weight methanol and an excess of methanol, distills off from column 1 and flows to condenser 6. The bottom liquid from column 1, containing MIBK and impurities, drops into tank 7.

After the overhead vapor has been condensed by condenser 6, the condensate drops into tank 8. Part of the condensate returns to the rectifying column 1 as reflux at a rate of reflux ratio of 10 to 15. The remainder of the condensate is sent by pump 9 to the bottom of the extraction column 10. Individual solvent is isolated within the column by countercurrent extraction with water introduced at the top of column 10 in the proportion of 2 parts of water to 1 part of azeotrope, by weight. The lower stream, as extract containing methanol and water, goes to tank 11 while the upper stream, as raffinate containing toluene and a small quantity of methanol and water, flows to tank 12.

The recovery of pure solvent from each of these streams, extract and raffinate, is done by fractional distillation with rectifying column 13 and auxiliary equipment including pumps 14 and 15, heat exchangers 16 and 17 and tanks 18, 19, and 20 by much the same procedure as already described, with the following process conditions. Using heater 16, the preheated temperature is 65° C. for the extract stream and 85° C. for the raffinate stream. The column 13 is shorter than column 1, approximately 10 theoretical plates. The methanol is distilled from the raffinate as a methanol-toluene azeotrope that after condensation with condenser 17 is stored in tank 20 for further processing. The toluene-water bottom from column 13 is sent to tank 19 by pump 28. The water bottom in tank 19 is sent to disposal, while the upper layer is pure toluene. Similarly methanol is recovered from the extract stream by distillation in the same column 13 as overhead which, after condensation with condenser 17, is collected in tank 18 where the solvent will finally go to storage. The water bottom from column 1 is sent to waste disposal.

MIBK is recovered from the bottom liquid in tank 7 by azeotropic distillation in column 21 with live steam. The liquid steam is sent by pump 22 into heater 23 and preheated to 88° C. before entry into column 21. Overhead from column 21, containing an azeotrope of MIBK and water, passes through condenser 24 where it condenses by cooling with water and drops into tank 25 forming two layers. The lower water-rich layer is returned to column 21 as reflux. The upper MIBK-rich layer, after further cooling in cooler 26, flows into tank 27. The column 21 bottom containing water and impurities is sent to waste disposal.

Although this invention has been disclosed and described herein with reference to a process for the separation and recovery of spent liquor from a pharmaceutical process, it is intended to be utilized for any solvent mixture or solution regardless of source. More specifically, this process invention may be used to isolate solvents having boiling temperature differences of 10° C. or less relative to the azeotrope. Further, this process is not limited to a continuous process which will require a steady supply of substantial amount of spent liquor. For small scale operation, a batch process has an advantage of reducing the number of equipments of the same process function.

Other modifications of the invention may be made without departing from the spirit of the invention as set forth in the appended claims.

What is claimed is:

1. In a distillation process for separating a mixture of methyl isobutyl ketone (MIBK) and toluene, the improvement which comprises adding methanol to the mixture prior to distillation to form an azeotrope of toluene and methanol and then distilling the mixture to separate and recover one fraction of the MIBK and another fraction of said azeotrope.

2. The process of claim 1 wherein at least about 2.62 parts by weight of methanol is added per 1.0 part by weight of toluene.

3. The process of claim 1 wherein the methanol is added to the spent liquor mixture in an amount at least sufficient to form an azeotrope with all of the toluene present in the mixture.

4. The process of claim 1 wherein the methanol is added to the spent liquor mixture in excess of the amount sufficient to form an azeotrope with all of the toluene present in the mixture.

5. The process of claim 1 wherein the methanol is added to the spent liquor mixture in an amount of from about 3.4 to about 6.3 parts by weight of methanol per 1.0 part by weight of toluene.

6. The process of any of claims 1, 3, 4 5 or 2 wherein the methanol is separated and recovered from the azeotrope by extraction with water.

7. The process of claim 5 wherein all of the methanol, including the excess and the azeotrope amount, is recovered by extraction with water.

8. An azeotropic distillation process for separating a mixture of MIBK and toluene, which process comprises adding methanol to the mixture in an amount sufficient to form an azeotrope with all of the toluene present in the mixture and then distilling the mixture to separate the azeotrope and the MIBK.

9. The process of claim 8 wherein the methanol is added to the spent liquor mixture in excess of the amount sufficient to form an azeotrope with all of the toluene present in the mixture.

10. The process of claim 8 wherein the methanol is added to the mixture in an amount of from about 3.4 to about 6.3 parts by weight of methanol per 1.0 part by weight of toluene.

11. The process of any of claims 8, 9 or 10 wherein the methanol is separated and recovered from the azeotrope by extraction with water.

12. The process of claim 9 wherein all of the methanol, including the excess and the azeotrope amount, is recovered by extraction with water.

* * * * *